United States Patent [19]

Spector et al.

[11] Patent Number: 4,756,862

[45] Date of Patent: Jul. 12, 1988

[54] PROSTHETIC DEVICES HAVING COATINGS OF SELECTED POROUS BIOENGINEERING THERMOPLASTICS

[75] Inventors: Myron Spector, Charleston, S.C.; George T. Kwiatkowski, Greenbrook, N.J.; Walter H. Smarook; Michael J. Michno, Jr., both of Somerville, N.J.

[73] Assignee: Amoco Corporation, Chicago, Ill.

[21] Appl. No.: 878,515

[22] Filed: Jun. 23, 1986

Related U.S. Application Data

[60] Continuation of Ser. No. 614,374, May 24, 1984, abandoned, which is a continuation of Ser. No. 417,586, Sep. 13, 1982, abandoned, which is a division of Ser. No. 113,317, Jan. 18, 1980, Pat. No. 4,362,681, which is a continuation-in-part of Ser. No. 377, Dec. 29, 1978, abandoned, which is a division of Ser. No. 787,531, Apr. 14, 1977, Pat. No. 4,164,794.

[51] Int. Cl.⁴ ............................................. A61F 1/24
[52] U.S. Cl. ....................................... 264/126; 623/11
[58] Field of Search ........................... 264/126; 623/11

[56] References Cited

U.S. PATENT DOCUMENTS

| 3,102,300 | 9/1963 | Rottig | 264/126 |
|---|---|---|---|
| 3,297,805 | 1/1967 | Rottig | 264/126 |
| 3,354,249 | 11/1967 | Zehender | 264/126 |
| 3,413,394 | 11/1968 | Jordan | 264/126 |
| 3,642,970 | 2/1972 | Hagitan | 264/126 |
| 3,975,481 | 8/1976 | Baurmgartuer | 264/126 |
| 3,986,212 | 10/1976 | Sauer | 128/92 C |
| 3,987,137 | 10/1976 | Neuman | 264/126 |

FOREIGN PATENT DOCUMENTS 929314 7/1973 Canada ............................ 264/126

OTHER PUBLICATIONS

B. W. Sauer, The Role of Porous Polymeric Materials in Prosthesis Attachment, Clemson University, Biomaterials Symposium, Apr. 14–18, 1973.

M. Spector et al., Bone Growth into Porous High-Density Polyethylene, J. Biomed. Mater. Res. Symposium, No. 7, pp. 595–603 (1976).

Williams & Roaf, Implants in Surgery, W. B. Saunders Co., Ltd., Jul. 3, 1973, pp. 89–93.

Primary Examiner—Sam Silverberg
Attorney, Agent, or Firm—Donald M. Papuga; William H. Magidson; Ralph C. Medhurst

[57] ABSTRACT

Prosthetic devices, such as orthopedic, dental and maxillofacial prostheses, are provided which are composed of an inner load bearing, functional component and an outer foamed or sintered porous coating of selected bioengineering thermoplastics. The bioengineering thermoplastic coating is provided in regions where long-term bone fixation is desired by tissue ingrowth. The coatings offer substantial biomechanical advantages over any material system previously reported. Also provided, are anatomically shaped devices comprised totally of bioengineering thermoplastics with select porous areas; these devices include bone gap bridges, bone caps, and alveolar ridge augmentation implants.

2 Claims, 2 Drawing Sheets

PROSTHETIC DEVICES HAVING COATINGS OF SELECTED POROUS BIOENGINEERING THERMOPLASTICS

This application is a continuation of prior U.S. application Ser. No. 614,374, filed May 24, 1984, abandoned, which is a continuation of application Ser. No. 417,586, filed Sept. 13, 1982, abandoned, which is a divisional of application Ser. No. 113,317, filed Jan. 18, 1980, now U.S. Pat. No. 4,362,681, which is a continuation-in-part of application Ser. No. 000,377, filed Dec. 29, 1978, abandoned, which is a divisional of application Ser. No. 787,531, filed Apr. 14, 1977, now U.S. Pat. No. 4,164,794.

This invention relates in general to prosthetic devices having coatings of selected porous thermoplastics, which provide an optimum biomechanical environment for fixation of devices by a bone ingrowth mechanism. In one aspect, this invention relates to the use of certain intermediate modulus thermoplastics and fiber reinforced thermoplastics as porous coatings for regions of prosthetic devices where long-term bone fixation is desired by tissue ingrowth. In a further aspect, this invention is directed to a process for coating prosthetic devices with selected porous bioengineering thermoplastic materials.

Prior to the present invention various methods have been disclosed in the literature for the attachment of prosthetic devices to the musculoskeletal system. These methods can be categorized as involving: (1) impaction: (2) nails and screws; (3) cement; and (4) porous surface materials. The use of porous surface implants for fixation has been recognized as potentially providing significant advantages, however, this technique has not been accepted by the surgical community because of problems of early fixation and long term stability associated with prior art devices. Prior art inventions include U.S. Pat. No. 3,986,212 which issued Oct. 19, 1976 to B. W. Sauer describing "improved" composite prosthetic devices containing a porous polymeric coating for bone fixation by tissue ingrowth. The porous polymeric materials which are indicated to be useful are those having a specified density and interconnected pores of a specific average pore diameter. Among the polymeric materials disclosed are high density polyethylene and polypropylene or mixtures thereof having certain critical parameters. It is also indicated that the coatings can be mechanically interlocked or chemically bonded to the device.

U.S. Pat. No. 3,971,134 which issued July 27, 1976 to J. C. Bokros relates to a dental prosthesis for permanent or prolonged implantation in a jawbone of a living body. The implant can be coated with such materials as vinyl polymers e.g., acrylic polymers, polyethylene and carbon fiber filled Teflon.

J. Galante, et al, in J. Bone and Joint Surgery, 53A, No. 1, 101 (1971) describes sintered fiber metal composites as a basis for attachment of implants to bone and U.S. Pat. No. 3,808,606 which issued on May 7, 1974 to Raymond G. Tronzo describes stainless steel and cobalt-chromium-molybdenum alloy prosthesis possessing porous surfaces for fixation by tissue ingrowth.

Also, of general interest are U.S. Pat. No. 3,992,725 "Implantable Material and Appliances and Method of Stabilizing Body Implants", which issued on Nov. 23, 1976 to C. A. Homsy, U.S. Pat. No. 3,909,852 "Implantable Substitute Structure for at Least Part of the Middle Ear Bony Chain" which issued Oct. 7, 1975 to C. A. Homsy, and U.S. Pat. No. 3,971,670 "Implantable Structure and Method of Making Same" which issued July 27, 1976 to C. A. Homsy.

In addition to patents, various articles have appeared in the literature relating to bone ingrowth into porous materials. Typical articles include, among others, S. F. Hulbert, "Attachment of Prostheses to the Musculoskeletal System by Tissue Ingrowth and Mechanical Interlocking", J. Biomed. Mater. Res. Symposium, 4, 1 (1973Z); M. Spector, et al, "Bone Growth into Porous High-Density Polyethylene", J. Biomed. Mater. Res. Symposium, 7, 595 (1976); C. A. Homsy "Implant Stabilization—Chemical and Biochemical Considerations", Orthopedic Clinics of North America, 4, No. 2, 295 (1973) and J. N. Kent, et al, "Proplast in Dental Facial Reconstruction", Oral Surgery, Oral Medicine, Oral Pathology, 39, No. 3, 347 (1975).

However, the porous materials disclosed in the literature as being useful for prosthetic devices provide inappropriate biomechanical environments leading to either of two undesirable situations. First, low modulus-high creep porous coatings such as porous Teflon/graphite composites, exhibit metastable fibrous tissues in the pores after extended periods. This tissue is not suited to support load bearing joint prostheses. The fibrous tissue is a metastable precursor to bone and under normal physiological conditions (including physiological loading conditions) would remodel to bone. The high loads transmitted through low modulus materials and the excess creep result in fibrous tissue which fail to remodel to bone. Other low modulus-high creep materials employed for prosthetic devices include polyethylenes and polypropylene.

Secondly, high modulus materials such as ceramics ($16 \times 10^6$ psi) and metals like titanium ($17 \times 10^6$ psi) and cobalt-chromium-molybdenum alloy ($34 \times 10^6$ psi), do not spread sufficient load to the ingrown or surrounding bone to prevent resorption. In porous metal and ceramic coated femoral and humeral stems, load is concentrated at the apex of these prosthetic components causing stress concentrations in the surrounding bone and subsequent resorption. In addition, the bone spicules in the pores of these porous ceramic and metallic implants do not experience loads, thereby resorbing. The loss of bone from the pores in areas of porous implants which experience no load has been demonstrated histologically. This type of bone loss leads to a decrease in composite strength (e.g. interfacial shear strength) and a subsequent decrease in "in use" performance in these high modulus porous materials.

The above-cited patents and literature describe the use of porous coatings on prostheses and described acceptable pore size range requirements. However, it has been found that metals, ceramics and polymers such as the vinyl polymers, polyethylene, polypropylene, carbon filled Teflon and others disclosed as being useful for coating prosthetic devices do not establish the proper biomechanical environment to achieve appropriate early fixation, long-term stability and strength at the bone-prosthesis interface. Previously described polymeric materials can also lack the toughness, creep resistance, tensile and impact strength and steam sterilizability to be acceptable as the polymer of choice for coating prosthetic devices. Even select high density polyethylene and polypropylene porous compositions, stated to possess the right amount of flexibility and strength in U.S. Pat. No. 3,986,212 are deficient as will be discussed below.

The bone ingrowth in porous orthopedic implants can be considered as a two stage phenomenon. Each stage is influenced by the pore characteristics and biomechanical characteristics of the implant. In the first stage and immediately after implantation the porous component fills with a blood clot which subsequently becomes "organized". Fibroblasts appear in the clot region and fibrogenesis occurs. The clot is replaced by loose connective tissue and capillaries. At this point preosteoblasts begin to appear in the peripheral pores of implant. These cells can become osteoblasts or chondroblasts depending upon the environment. If the original pore size of the implant is too small or if the pore structure has been distorted by the initial applied loads as will occur with Teflon, high density polyethylene and polypropylene porous materials, one or more of the above sequence of events can be interrupted. For example, it is generally believed that a smaller pore size ($<90\mu$) leads to the ultimate formation of fibrous tissue, not bone, in the implant. If the modulus of the material is too low, micro-motion occurs with loading. This would lead to an environment that is conducive to fibrous or cartilage tissue, not bone, formation. For example, excessive motion can lead to disruption of vascularity and a decrease in oxygen, a condition which favors cartilage formation.

After bone has filled the pores of the implant, in the second stage it undergoes remodeling which is influenced primarily by its biomechanical environment. Spicules in the implant which experience uniform stress will thicken while those spicules which experience no stress or excessive stress (stress concentration) are resorbed. The modulus of metals and ceramics is so high that the implants do not deform under the applied loads. The bone spicules in these porous implants thus do not experience sufficient load to thicken. Bone trabeculae in these higher modulus porous materials tend to resorb, becoming thinner than the spicules in the porous implants which are the subject of this invention.

The above discussion indicates that the biomechanical environment established by the implant material and the geometry of the porous substrate have a profound effect on the biological fate of implants. It has now been found that certain thermoplastics, hereafter described as a class as bioengineering thermoplastics, provide the delicate balance which must be achieved between parameters affecting load transmission, micro-motion, dimensional stability, and strength. Bioengineering thermoplastics, usually prepared by condensation polymerizations, also show low metal contamination levels (i.e., Low transition metal catalyst levels) and exhibit excellent characteristics in biotoxicity studies such as the U.S. Pharmacopeia Class VI Standards. They represent an optimum materials category for orthopedic, dental and maxillofacial applications. The transmission of stress to bone in the pores of bioengineering thermoplastics mimics the physiological biomechanical environment as evidenced by the replication of the normal bone repair processes. Bone in porous bioengineering thermoplastic implants remodels after a clinically appropriate period to reflect the magnitude and direction of the prevailing stresses at the anatomical site. This occurrence permits the ingrown bone to be a structurally efficient member for the load environment to which a prosthesis is subjected.

It is, therefore, an object of the invention to provide efficacious prosthetic devices comprised of an inner load bearing functional component and an outer foamed or sintered porous coating over at least a portion thereof, of selected bioengineering thermoplastics. Another object of this invention is to provide coated prosthetic devices which after implantation achieve a long-term bone fixation by ingrowth of tissue into and through a select porous bioengineering thermoplastic coating with subsequent remodelling to bone. A further object is to provide a prosthetic device having a coating of a specified porosity which provides the optimum substrate for tissue ingrowth. Another object is to provide prosthetic devices wherein the coating exhibits sufficient tensile and impact strength during and after bone formation to accommodate applied loads during insertion and after surgery. A further object is to provide coated prosthetic devices which can undergo steam sterilization without adverse effects on the coating. A still further object of this invention is to provide anatomically shaped porous structures of select bioengineering thermoplastics which are useful for reconstructive procedures. Another object of this invention is to provide porous bioengineering thermoplastic coatings or structures containing additives for enhancement of their biological and/or mechanical properties. A further object of this invention is to provide porous bioengineering thermoplastic coatings or structures containing additives for increasing wear and abrasion resistance. Another object is to provide one or more processes for preparing coated prosthetic devices or anatomically shaped structures composed of bioengineering thermoplastics. The importance of these and other objects will readily become apparent to those skilled in the art in the light of the teachings herein set forth.

In its broad apsect the present invention is directed to prosthetic devices comprised of or coated with porous bioengineering thermoplastic materials which enables such devices to become firmly and permanently anchored into the musculoskelatal system by tissue ingrowth into the coated material. In one embodiment the prosthetic devices are comprised of a load bearing functional component and over at least a portion thereof, a porous coating of from about 0.5 to about 10 millimeters in thickness of a bioengineering thermoplastic material which is compatible with, and conducive for, the ingrowth of cancellous and cortical bone spicules, the coating having the following properties:

(a) an average pore diameter of from about 90 to about 600 microns;

(b) pore interconnections having average diameters of greater than about 50 microns;

(c) a modulus of elasticity from about 250,000 to about 3,000,000 pounds per square inch for the neat thermoplastic material or the reinforced thermoplastic material;

(d) a porosity of greater than about 25 percent; and, (e) a total creep strain of less than one percent at a constant stress of 1,000 pounds per square inch at ambient temperature, all of the properties being sufficient to enable stresses applied on the muscloskeletal system to be transferred to bone spicules within the pores and maintain sufficient load and pore stability to promote irreversible ossification.

Hence, it has been observed that the materials used in coating the load bearing functional component of prosthetic devices must possess specific properties if long-term bone fixation is to be achieved. Prosthetic devices prepared in accordance with the teachings of this invention have been found to provide the biomechanical environment necessary to uniformly transmit the proper magnitude of applied loads promoting the desired remodelling of bone trabeculae.

As previously indicated, the materials employed in the preparation of the prosthetic devices of this invention are classified as "bioengineering thermoplastics". One important feature of these materials is that their performance can be predicted by the use of metal design engineering equations for both long and short-term. These engineering design equations only apply up to the linear viscoelastic limit of the material. High density polyethylene has a linear viscoelastic limit of less than 0.1 percent and with this limit on the amount of strain, the allowable stress is minimal. In contrast, the linear viscoelastic limit of bioengineering thermoplastics, within the definition of this disclosure, is at least 1 percent strain. For example, one of the preferred engineering thermoplastic materials found to be suitable for the coatings of this invention is a polysulfone which has a 2 percent strain limit. Hence, the metal engineering design equations for both long and short term can apply up to this limit.

The unique characteristics of the bioengineering thermoplastic materials are more clearly evident when their performance is compared to polymeric materials previously disclosed as being useful for porous fixation devices. If the creep modulus extensively varies with time, deflection increases markedly, causing micro displacement of a prosthesis under load and pore distortion. Creep tests have already been reported in the literature on porous high density polyethylene and a polytetrafluoroethylene-graphite composite, both of which have been indicated in the previously cited patents. It has been observed that significant changes in pore structure occurred upon compressive stresses as low as 80 psi for the porous polytetrafluoroethylene-graphite composites and at 300 psi for the porous high density polyethylene. Typical time to failure versus stress for the two reported high density polyethylene fabrications were under five minutes when stress levels greater than 300 psi were applied. It should be noted that this represents the stress levels that will be experienced in some orthopedic joint and device applications. The importance of maintaining pore geometrics under loading environments was indicated earlier where it was observed that fibrous tissue is created in small pores. This is particularly critical in early post-operative periods prior to the ingrowth of bone when the porous polymeric coating on joint prostheses must have sufficient strength and rigidity to independently support applied load without assistance from ingrown bone. The strength of prior polymeric materials comes from the ingrown bone. Bioengineering thermoplastic porous coating have strength like bone.

Illustrative prosthetic devices which are within the scope of the teachings of this invention are readily apparent from the following description and from the accompanying drawings wherein.

Figure 1:
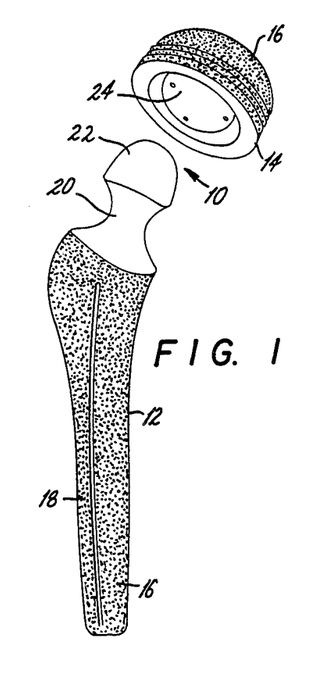
FIG. 1 is a plan view of the stem and ball portion of a total hip prosthesis having a coating of a porous bioengineering thermoplastic material.

Referring now to FIG. 1 of the accompanying drawings, the total hip prosthesis 10 is comprised of ball and stem member 12 and cup member 14. The stem portion of the ball and stem member 12 is coated over its entire surface with a porous bioengineering thermoplastic coating 16 of this invention. Although the stem portion is depicted in FIG. 1 as a solid stem with a groove 18 along at least a portion of its length, it can have openings, ridges or other configurations to provide coated sites for tissue growth to firmly anchor it to the skeletal system. Cup member 14 is likewise coated on its exterior surface with the porous engineering thermoplastic 16. The neck 20, ball 22 and inner surface of the cup 24 do not, of course, contain any coating.

Figure 2:
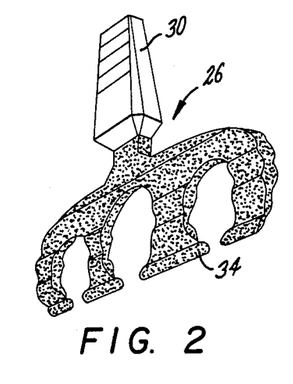
FIG. 2 is a plan view of an endosteal blade implant having a coating of a porous bioengineering thermoplastic material on the blade portion thereof.
Figure 3:
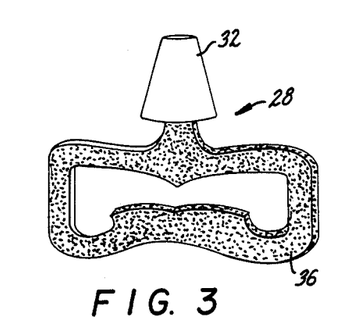
FIG. 3 is a side plan view of another endosteal implant having the blade portion coated with the porous bioengineering thermoplastic material.

FIGS. 2 and 3 of the drawings depict commercially available implants 26 and 28 which can be fabricated in a variety of shapes and are designed for supporting groups of artificial teeth These devices are usually comprised of cobalt or titanium alloys and are inserted into slots cut into the alveolar ridge. The posts 30 and 32 protrude into the oral cavity and are used for anchoring the artifical teeth. As shown in the drawing, the stem portions 34 and 36 can be coated with the porous bioengineering thermoplastic material and provide for bone ingrowth to firmly affix the prosthesis in the alveolar ridge.

Figure 4:
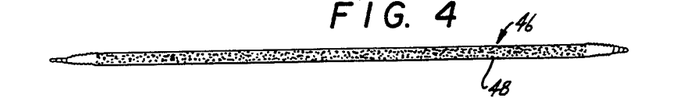
FIg. 4 is a side plan view of a self-broaching intramedullary nail having a coating over its entire length of the porous bioengineering thermoplastic material.
Figure 5:
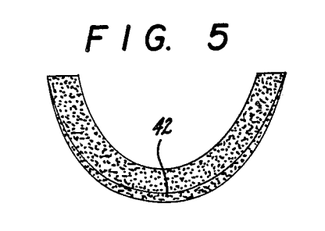
FIG. 5 is a plan view of a prosthetic device comprised entirely of a porous bioengineering thermoplastic material.

An intramedullary nail 38 is illustrated in FIG. 4 and has a coating 40 of the porous bioengineering thermoplastic material over its entire length. These nails are placed in the medullary canal of long bones, such as femurs, and are usually limited to the middle one-third section of such bones. These nails are wedged lengthwise into the medullary canal and press against the interior of the cortex. Finally, FIG. 5 provides a plan view of a porous implant 42 which can be used for alveolar ridge reconstruction. Thus, ridge reconstructions can be made by using a porous or solid interior bioengineering thermoplastic implant, without a load-bearing functional component, carved or molded to the desired anatomical shape.

Figure 6:
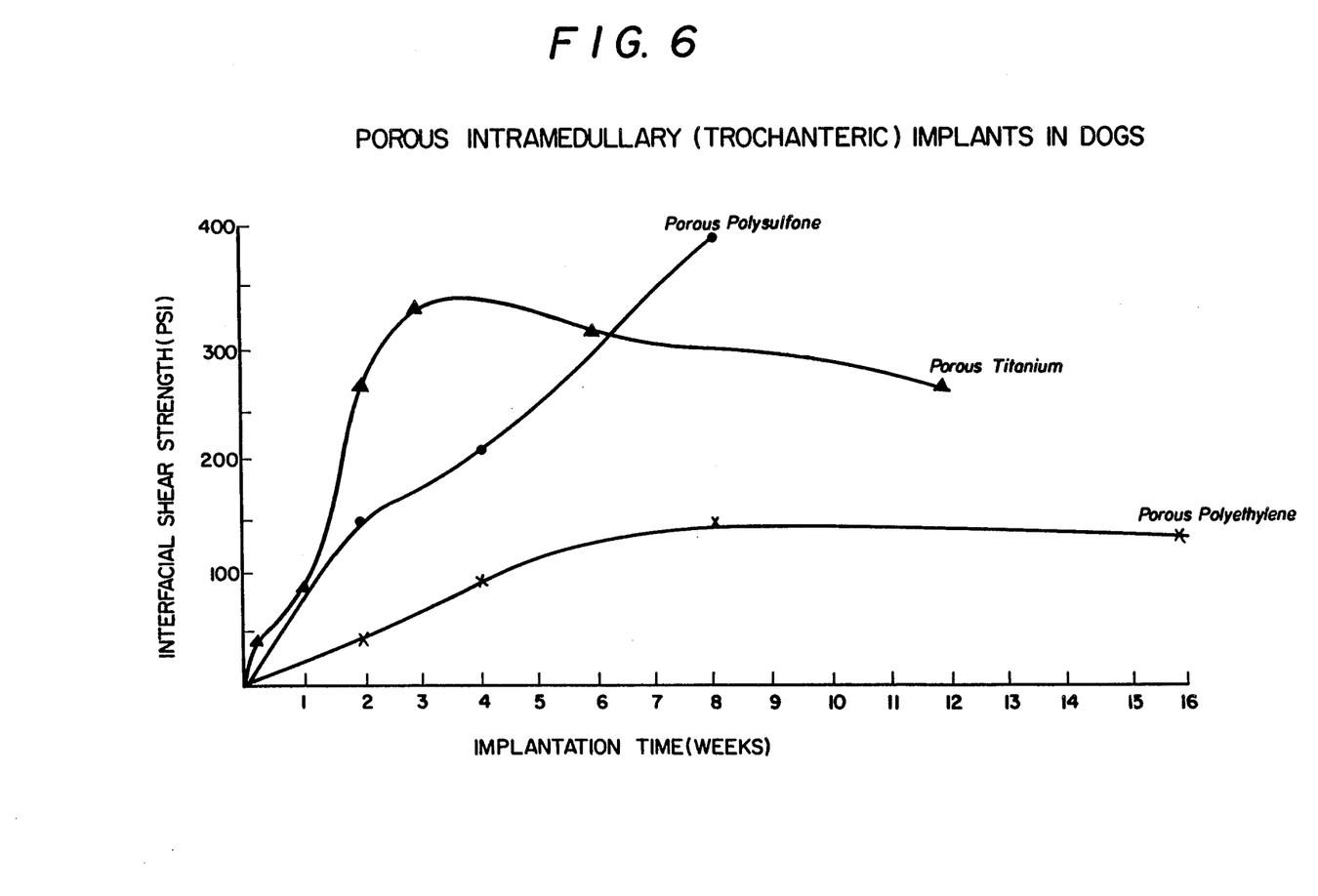
FIG. 6 is a graph depicting the relationship of interfacial shear strength versus implantation time of several porous materials.

FIG. 6 is a graph depicting the relationship of interfacial shear strength in pounds per square inch versus time in weeks for trochanteric implanted intramedullary rods of porous polysulfone, porous titanium and porous polyethylene. The porous polysulfone was prepared in accordance with the teachings of this invention and exhibited the physical characteristics previously described for bioengineering thermoplastics. The data for the porous titanium and polyethylene implants was reported by other investigators. In each case, the rods were implanted in dogs in accordance with accepted surgical techniques.

While each of the tests was performed in a similar fashion in dogs, there is the possibility that the results could vary somewhat because of differences in implantation and mechanical testing procedures used by the different investigators. However, these variations are not great enough to prevent comparison. Of particular interest is the fact that the interfacial shear strength of porous polysulfone is high enough after only two weeks (1150 psi) to support the static load and most dynamic loads that might be placed upon a hip prosthesis by a patient immediately after surgery. This type of data thus evidences the possibility of early weight-bearing post-operatively for polysulfone, whereas the porous high density polyethylene exhibits an interfacial shear strength value only one-third that of polysulfone. Indeed, only after extended implant periods, did the high density polyethylene come up to the two week value for polysulfone, and it fell short of the ultimate shear strength value for polysulfone.

As hereinbefore indicated, the materials which are employed in the present invention are designated as bioengineering thermoplastics. These materials are unique in that they combine melt processability with structural strength, rigidity, creep resistance, toughness, and steam sterilizability. Incorporation of glass, carbon or organic based fibers into the bioengineering thermoplastics extends the load-bearing and structural characteristics. Bioengineering thermoplastics exhibit bulk tensile or flexural modulus values in the range of 250,000–500,000 psi. Fiber reinforced products exhibit modulus values up to 3.0 million depending on the fiber type and loading. These values of modulus provide the intermediate range required for initial post-operative support and long-term stability of implanted prostheses in high load areas anchored by bone ingrowth.

Each of these materials when prepared in accordance with the teachings of this invention provides coatings or free standing articles having the physical properties hereinbefore enumerated. Illustrative of these materials are the polysulfones, such as, polyphenylsulfone, polyethersulfone, polyarylsulfones, and the like; polyphenylenesulfide, polyacetal, thermoplastic polyesters such as the aromatic polyesters polycarbonates; aromatic polyamides, aromatic polyamideimides, thermoplastic polyimides and the polyaryletherketones, polyarylethernitriles, aromatic polyhydroxyethers, and the like. The most preferred materials for use in the invention are the aromatic polysulfones. These polysulfones contain repeating units having the formula:

[Ar—SO₂]

wherein Ar is a divalent aromatic radical containing at least one unit having the structure:

in which Y is oxygen, sulfur or the radical residuum of an aromatic diol, such as 4,4'-bis(p-hydroxyphenyl)-alkane. Particularly preferred polyarylene polyether polysulfone thermoplastic resins are those composed of repeating units having the structure shown below:

wherein n equals 10 to about 500. These are commercially available from Union Carbide Corporation as UDEL Polysulfones P-1700 and P-3703. These materials differ in that P-3703 has a lower molecular weight. Also useful are Astrel 360 a polysulfone sold by 3M Corporation and Polysulfone 200 P sold by ICI and Radel polyphenylsulfone sold by Union Carbide Corporation. Certain crystalline bioengineering thermoplastics like Stilan from Raychem Corporation, Polyarylene and Phenoxy A from Union Carbide Corporation, are also useful.

In practice, the prosthetic devices of this invention having an inner load-bearing functional component or those existing as free standing anatomically shaped devices are conveniently prepared by one or more methods. In one method the coating or article can be formed by a sintering technique whereby particles of the bioengineering thermoplastic material are heated for a period of time and at a temperature sufficient to cause sintering that is, the particles fuse together at one or more contact points to provide a porous continuous composite material of the bioengineering thermoplastic. In a second method, the coating or article can be formed by a process which involves the formation of a low density foam of the normally solid thermoplastic material. This second method which can be described as the dough foam technique is particularly useful for the preparation of the porous materials. However, its use is limited to the aforementioned polysulfones and phenoxy A aromatic polyhydroxyethers.

Porous bioengineering thermoplastic coatings and blocks prepared by these methods exhibit intermediate modulus values, high strength and high creep resistance. They can uniquely be fabricated with high total porosities and pore sizes, while still meeting the strength and biomechanical criteria observed to be necessary for bone repair and prosthesis fixation/stabilization. For example, sintered polysulfone having an average pore size of 200 microns and a 53 percent porosity, had a flexural strength of 2000 psi and flexural modulus of 60,000 psi.

Foamed specimens with a 70 percent porosity had a flexural modulus of about $10^5$ psi. This value increased to $8 \times 10^5$ psi with the introduction of 30 weight percent carbon fibers.

With respect to the first method, it has been observed that through careful control of temperature, time and pressure, all bioengineering thermoplastics can be sintered. For example, UDEL-P-1700 polysulfone can be satisfactorily sintered at approximately 245° C. and Radel polysulfone is generally sintered at approximately 285° C. At appropriate temperatures, times and pressures the other thermoplastic materials can also be sintered to provide a porous product suitable for the intended use. It has been observed, however, and particularly for use in preparing the coatings and articles of this invention, that optimum properties can be obtained in a unique and facile manner by proper choice of both (a) particle size and (b) molecular weight distribution.

As indicated previously, the desired properties are exhibited by the prosthetic device when the bioengineering thermoplastic material has a porosity of about 50 percent and more preferably from about 40 to about 70 percent. Porosity is influenced by the particle size employed in the sintering operation. Particle size also influences the strength of the porous sintered materials. Large particles result in large pore sizes, while small particles improve strength by increasing the fusion area of the particles.

It has been observed that the modulus of a porous material can be predicted through the Kerner equation or through a modified Halpin-Tsai equation. Hence, in order to achieve a material with a porosity, for example, of 55 percent, and an elastic modulus greater than 40,000 psi, the modulus of the starting polymer must exceed 200,000 psi. Thus, most polypropylenes, and all high density polyethylenes are incapable of being fabricated in a material of 55 percent porosity with a modulus of 40,000 psi. On the other hand since the modulus of solid polysulfone exceeds 340,000 psi, a material of 55 percent porosity whose modulus exceeds 70,000 psi can be obtained.

Even though it was possible to predict the modulus of a thermoplastic having a desired porosity there was no simple method available to fabricate a material approaching these predictions which would be useful for the devices of this invention. It was unexpectedly found, however, that the desired degree of porosity could be obtained without sacrificing mechanical properties by the proper choice of particle size, molecular weight distribution and sintering conditions. All three are inter-related and necessary to achieve a coating or article having the necessary characteristics. For example, the sintering time and temperature which results in a desired pore size distribution may not produce the desired modulus of elasticity and/or tensile strength. Starting particle size distribution, sintering time, and temperature must be adjusted to achieve the desired balance of pore size, porosity, and mechanical properties.

With respect to particle size distribution, a blend of two or more different sizes of the bioengineering thermoplastic material was found to provide a sintered material which best met the porosity and mechanical requirements needed for a successful prosthetic device.

In practice, a mixture of particle sizes wherein the ratio of particle diameters ranges from about 7:1 to about 5:1 has been found to be acceptable. Particle sizes of from about 300 microns to about 50 microns are particularly preferred. For example, a mixture of particles which are retained on a 50 mesh screen (U.S. Standard Sieve) and pass through a 270 mesh screen have provided coatings and articles having the desired porosity and biomechanical features. It has also been observed that optimum results are achieved when the particle size distribution ranges from about 40 to about 60 weight percent.

As indicated, the sintering conditions are also important to achieve the desired properties. Sintering has been accomplished by charging a metal mold with powder and heating the mold to a prescribed sintering temperature, $T_s$, greater than the glass transition temperature, $T_g$, and less than the melting or melt processing temperature, $T_m$, (i.e. $T_g < T_s < T_m$). The sintering temperature is held constant for a given time, t. Essentially, no pressure, other than that induced by differential thermal expansion, is applied. The application of pressure at $T_s$ leads to fluxing of the material. This indicates that if pressure is applied, lower temperatures and shorter time cycles must be employed to retain porosity in the sintered parts. Experiments were run and set forth in the examples to delineate the effects of the sintering conditions on the pore size, porosity, and tensile properties of the porous sintered plastic for various powder size and molecular weight distributions.

In a second method it has been found that since some bioengineering thermoplastics are soluble in low-boiling organic solvents a solvent foaming technique can be utilized for molding open cell porous foam coatings onto protheses or for the preparation of foamed articles. Porous foamed coatings and articles offer advantages over sintered porous coatings and articles in that higher porosities can be achieved at higher strengths, due to the thin contiguous pore walls obtained in the foaming processes. Further, low fabrication temperatures are experienced due to the plasticizing effects of the solvent on the thermoplastic. This technique is not amenable to Teflon, polyethylene or polypropylene being described as preferred materials in prior art patents.

This solvent foaming technique for fabricating low density, foamed articles comprises the steps of:

(a) blending at least one normally solid bioengineering thermoplastic with about 25 to about 80 parts, per 100 parts by weight, of a normally liquid organic solvent having a solubility parameter, $\delta$, within $(1.3 \text{ calories per cc})^{\frac{1}{2}}$ of that of the thermoplastic, or a mixture of normally liquid organic solvents having the same solubility parameter;

(b) blending the mixture obtained in step (a) with at least about 1 part by weight, per hundred parts of thermoplastic, of water whereby a non-tacky hydrogel dough is obtained;

(c) shaping the hydrogel dough obtained in step (b);

(d) vaporizing the solvent and water and (e) recovering a foamed resin article.

It has been found that foam prepared in this manner posseses the desired degrees of both porosity and biomechanical properties.

It has been observed, however, that the values of the solubility parameters of the normally liquid organic solvents used are fairly critical as evidenced by the fact that with a preferred thermoplastic resin such as the polysulfone depicted above there is a distinct difference between structurally similar solvent isomers. Thus, for example, the above-described polysulfone, which has a solubility parameter calculated to be 10.55, is soluble in 1,1,2-trichloroethane having a solubility parameter of 10.18 but insoluble in 1,1,1-trichloroethane having a solubility parameter of 8.57. However, a mixture of organic solvents which individually is unsatisfactory can be used as long as the average solubility parameter of the mixture is within $(1.3 \text{ calories per cc})^{\frac{1}{2}}$ of the resin being blown. In addition, if the Tg of the polymer that is to be plasticized is exceptionally high in value, plasticity of the gel can be prolonged during the foaming step by forming a mixture of solvents, one of which should have a much higher boiling point value. Thus for example while ethanol or 1,1,1-trichloroethane cannot be used individually with the polysulfone depicted above a mixture comprising equal parts by volume of ethanol and 1,1,1-trichloroethane can be used. Other combinations which function as organic solvents for polysulfone are:

95% chloroform and 5% water,
85% methylene chloride, ethanol 20% and water 5%,

95% tetrahydrofuran and water 5%,
75% methylene chloride, 10% acetone, 10% ethanol, and 5% water, and
80% cyclohexanone, ethanol 15% and water 5%.

The amount of water added is not critical but generally at least 1 part is required per 100 parts by weight of resin. There is no maximum amount because excess water separates from the dough-like mass as a separate phase. Because of the phase separation, where the solvent employed is for the most part not miscible with the water phase, the excess water acts as a protective blanket which prevents rapid solvent loss from the plasticized polymer. This feature allows the plasticized polymeric gel to be exposed in an open vessel during handling and transfer without sealed containment. In this form the polymer blend can be easily transferred from one vessel or container to another and can be shaped and molded or otherwise worked without the necessity for using contaminating release agents. Simple mixing equipment known to those skilled in the art is all that is required to blend the water into the mixture of thermoplastic resin and liquid organic solvent. The resultant hydrogels can be used immediately or if desired stored indefinitely under water and then recovered and used without further treatment.

The organic solvent once it diffuses into polymer resin, serves two purposes, namely, the formation of a gel retaining a finite solvent concentration in a plasticized form and secondly the solvent serves as a blowing or foaming agent at a much lower temperature and viscosity than that which would be required to foam the original non-plasticized polymer resin with a conventional gaseous type blowing or foaming agent. At blowing temperatures of from 165°–200° C. necessary for polysulfones, most of the commonly used organic solvents diffuse out of the polymer blend too quickly to provide adequate blowing of the resin. During the blowing operation the water in the hydrogel is also removed with the normally liquid organic solvent. Thus while the second order transition temperature (Tg) of the polymer resin being treated in this manner is lowered, enhancing the processing of the polymer at lower temperature, the liquid organic solvent and the water being fugitive in nature, when removed from the polymer resin leave the foamed article with the physical properties of the original resin prior to processing. This is extremely important in the case of polymers which are difficult to process because of their viscoelastic and rheological properties or heat instability.

The wide latitude of conditions under which the foaming operation can be carried out in this process was also quite surprising. Thus for example, while one can practice the foaming step at higher temperatures, one can also operate at the other end of the spectrum, that is, at room temperature or by placing the hydrogel in a vacuum device, such as, a vacuum oven and with organic solvents of low volatility, such as, methylene chloride, readily remove the solvent and water in a relatively short time.

As previously indicated, another embodiment of this invention is directed to prosthetic devices which do not contain a separate inner load-bearing functional component but rely on the structural integrity of the bioengineering thermoplastic material itself. For example, a porous block can be carved to an anatomically appropriate shape, and used to augment atrophic mandibular alveolar ridges and deficient facial contours in the mental, mandibular border, and zygomatic areas. Other devices, can include bone gap bridges and bone caps (used to control bone overgrowth in amputees) which are either totally porous bioengineering thermoplastics, or bioenginnering thermoplastic coated metals or bulk polymers (reinforced and unreinforced. The alveolar ridge reconstruction augmentation device shown in FIG. 5 is prepared from a porous bioengineering thermoplastic composite by molding and/or carving a block of the composite to the desired shape.

The porous bioengineering thermoplastics can also be carved to anatomical shapes without destruction or collapse of the surface porosity. Bone gap bridges, bone caps and other pre-sized implants can be machined without destroying the porosity and surface of the porous engineering thermoplastics. Porous high density polyethylene, polypropylene, and the polytetrofluoroethylene creep and "feather" during carving and machining operations.

The high strength-low creep of the bioengineering thermoplastics and reinforced bioengineering thermoplastics also translate to the load-bearing components of prosthetic devices and implants. For this reason, prostheses can be developed incorporating a composite system of bioengineering thermoplastic load-bearing components and articulating surfaces, with porous bioengineering thermoplastic coatings in areas where attachment to the musculoskeletal system is desired. The bioengineering thermoplastics remain tough after being filled with reinforcing fillers, where polyolefins such as high density polyethylene become brittle at high fiber loadings. Bone gap bridges and joint prostheses demonstrate this principle.

Such implantables are rendered more useful because of the ability to achieve high interfacial strengths between the bulk load-bearing component and the porous coating when the identical materials are combined in the construction. These combinations are not achievable with polyolefins due to the poor structural characteristics of these materials, nor with ceramics or metals because of the biomechanical unsuitability of the respective porous coatings.

In joint prostheses where the bioengineering thermoplastic must also form the articulating surface, it is often desirable to incorporate additives which increase the wear and abrasion resistance of the composite. Carbon fiber, graphite fiber, teflon, molybdenum disulfide are useful additives which afford wear resistance engineering thermoplastics equal or superior to self-lubricated materials typically used in commercially available joint prostheses.

In journal bearing wear tests*, the following comparative results were obtained:

*Conditions ASTM-D1242—1400 hours, 110 ppm, 5 lbs. on level arm

| Sample | Weight Loss (grams) |
| --- | --- |
| Control HDPE | 0.0806 |
| Control polypropylene | 0.0404 |
| UDEL polysulfone | 0.2794 |
| UDEL with 20% carbon fiber | 0.0362 |
| UDEL with 20% graphite | 0.0324 |

Compositions with carbon fiber are preferred for the injection molding or machining of articulating prosthesis such as acetabular cups, tibial, and glenoid components of total knee and shoulder replacements.

In another embodiment of this invention silyl reactive polymers like silyl reaction polysulfone are utilized for bonding porous polymeric coatings to metal substrates. Silyl reactive polysulfone (PSF-SR) resins possess three important features. First, the presence of hydrolyzable silane end groups provides an inherent coupling ability to metallic surfaces. Second, the PSF-SR resins have a low melt (or solution) viscosity which greatly facilitates "wetting" during the formation of adhesive bonds. Third, they are polymeric adhesives which exhibit no solubility in physiological fluids and hence have no biological/toxicological effects when implanted.

The load bearing functional component of the prosthetic devices of this invention can be comprised of a variety of metals and alloys known in the art. While titanium and tantalum are, for the most part, the only pure metals considered as safe for internal use, a variety of alloys have found general acceptance. Stainless steels, cobalt-base alloys and titanium based alloys all are tolerated by the body as well as being corrosion resistant and fabricated into desired shape.

EXAMPLE I

Effect of Sintering Conditions on Pore Size

For this experiment simple molds were fabricated from ⅜ inch outer diameter steel tubing. The tubing was cut to a 6 inch length and fitted with threaded end plugs. Wall thickness of the tubing was approximately 0.038 inch. The resulting sintered plastic part had a diameter of 0.300 inch and was 6 inches long. This proved to be a convenient sample size for tensile property characterization.

PSF-3703 powder with the particle size distribution shown in Table I below was used. This material was sintered according to the following schedule: pack powder in a mold; immerse mold in an oil bath at 220° C. for various times ranging from 10 to 30 min. The resulting rod of 0.300 inch diameter was then cut to sample lengths of 2.5 inches.

Interconnecting pore size distribution was then determined through mercury intrusion porosimetry. Data are reported in Table I. Characteristic pore size is shown as the percentage of pores larger than or equal to 132μ. As the time at temperature is increased from 10 to 30 minutes, the number of pores ≧132μ in diameter increases. However, if the material is held at 220° C. for times greater than 30 minutes, the resulting sample would no longer be porous. On the other hand, if the material were exposed to temperature for less than 10 minutes, little or no sintering would have occurred. Thus, there is an optimum time at temperature and temperature for a given particle size and molecular weight distribution to achieve a desired pore size.

TABLE 1

| U.S. SCREEN | DISTRIBUTION |
|---|---|
| % on 35 | — |
| on 40 | Trace |
| on 50 | — |
| on 60 | 14.0 |
| on 80 | 50.0 |
| on 100 | 18.0 |
| thru 100 | — |
| on 140 | 10.0 |
| on 230 | 4.0 |
| thru 230 | 4.0 |

| Sintering Time at 220° C. (Min.) | % Pore Volume ≧132 μ |
|---|---|
| 10 | 49.4 |
| 12 | 52.6 |
| 14 | 56.5 |
| 16 | 58.1 |
| 18 | 61.8 |
| 20 | 69.5 |
| 30 | 75.4 |

EXAMPLE II

Effect of Molecular Weight on Sintering

The following experiment was conducted to demonstrate the effect of a low molecular weight tail upon sintering conditions and resulting mechanical properties. PSF-3703 was "plasticized" via the addition of 0.5 and 1.0 weight percent of diphenysulfone. Blending was accomplished in an Egan 1 inch laboratory extruder. The "plasticized" PSF was then ground into powder on a laboratory WEDCO grinder. The resulting powder was sintered into porous rods 0.300 inch diameter and 6 inches long. Tensile properties of the rods were measured.

Table II presents the mechanical properties for the porous materials after sintering for 20 minutes at various temperatures. The material containing 1 wt. % diphenylsulfone was weakly sintered at 200° C. while the other materials did not sinter at this temperature. In all cases, as the sintering temperature is increased, the "plasticized" material possesses superior mechanical properties in the porous sintered form. It is evident that addition of diphenylsulfone, (or similar low molecular weight species) provide a method to control sintering conditions. Specifically, shorter sintering time cycles at a given temperature or lower temperatures at a given time may be possible.

TABLE II

SINTERED PSI 3703 + DIPHENYL SULFONE - TENSILE AND PHYSICAL PROPERTIES

| Sample | % Added Diphenyl Sulfone | Time (min) | Temp. °C. | % Porosity | Tensile Strength PSI | Ultimate Strain % | Modulus of Elasticity PSI |
|---|---|---|---|---|---|---|---|
| 1 | 0 | 20 | 200 | 51 | —(1) | — | — |
| 2 | 0.5 | 20 | 200 | 51 | — | — | — |
| 3 | 1.0 | 20 | 200 | 52 | 36 | 0.30 | 12,000 |
| 4 | 0 | 20 | 210 | 52 | 102 | 0.80 | 15,200 |
| 5 | 0.5 | 20 | 210 | 52 | 134 | 0.76 | 21,600 |
| 6 | 1.0 | 20 | 210 | 53 | 127 | 0.71 | 20,600 |
| 7 | 0 | 20 | 220 | 51 | 481 | 1.78 | 35,600 |
| 8 | 0.5 | 20 | 220 | 52 | 556 | 1.40 | 48,800 |
| 9 | 1.0 | 20 | 220 | 51 | 684 | 1.50 | 55,600 |
| 10 | 0 | 20 | 230 | 50 | 1,170 | 1.80 | 80,900 |
| 11 | 0.5 | 20 | 230 | 52 | 1,310 | 2.30 | 75,900 |

TABLE II-continued
SINTERED PSI 3703 + DIPHENYL SULFONE - TENSILE AND PHYSICAL PROPERTIES

| Sample | % Added Diphenyl Sulfone | Time (min) | Temp. °C. | % Porosity | Tensile Strength PSI | Ultimate Strain % | Modulus of Elasticity PSI |
|---|---|---|---|---|---|---|---|
| 12 | 1.0 | 20 | 230 | 51 | 1,010 | 1.00 | 97,800 |

[1]Samples broke immediately - not possible to record data.

EXAMPLE III
Preparation of Porous Bioengineering Thermoplastic Coated Prosthesis The stem section of a Richards Manufacturing canine femoral component was dip coated in a 10 percent solution of PSF-SR/methylene chloride, air dried and baked at 110° C. for 1 hour. The stem section of the prosthesis was then dip coated with a 15 percent solution of P-3703/tetrahydrofuran and while tacky, dusted with powdered P-3703. The primed prosthesis was placed in a tapered aluminum mold whose cavity replicated the stem section of the femoral component, with a tolerance of 100 mil. The cavity was loosely packed with powdered P-3703, sealed at the bottom and placed in an oil bath at 215° C. for 24 minutes. After cooling, the prosthesis was removed. The stem section had a tightly adherent coating of porous polysulfone.

EXAMPLE IV
Preparation of Porous Bioengineering Thermoplastic Article

To 400 gms. of UDEL polysulfone P-1700 resin in a one gallon wide mouth jar was added 319.2 gms. of methylene chloride with agitation. The jar was sealed and allowed to stand at room temperature for 16 hours. A polysulfone/methylene chloride brown gel was obtained to which 558 gms of water were added with mixing. The brown gel turned white in color. These proportions formed a standard dough mix (SDM). A 30 g. portion of the SDM was shaped at room temperature by hand compression into a ⅜" aluminum metal plate 8"×8" having a circular hole measuring 4⅞" in diameter. The resultant dough preform was then inserted at 155° C. into a heated telescoping type aluminum mold consisting of an upper 5" aluminum disc, fastened to the upper platen of a press, which slides into a ring and meets another 5" aluminum disc within the ring. The ring and bottom disc were not fastened to the bottom platen of the press.

Upon insertion of the dough preform the press was closed allowing both disc mold surfaces to compress the preformed dough with a pressure of 50 psi. During the following 15-25 seconds a pressure build up occurs due to the volatilization of the solvents. The pressure builds up to 152 psi at which point the press was released slowly to maintain a pressure of 125 to 150 psi. The release of the pressure allows movement of the mold surfaces activating an expansion of the mold with subsequent release of solvent and water vapor from the mold and polymer expansion. During the dwell time in the mold continuous solvent and water vapor loss further reduces the pressure to about 50 psi or less. After a total of four minutes the mold was opened and the foamed disc was removed. The disc had smooth surfaces on both sides and had a density of 0.19 g. cc. the surfaces when machined revealed an open pore network and the disc could be cut to desired shapes.

EXAMPLE V
Shear Strength Measurements of Porous Bioengineering Thermoplastics Stainless steel plates 0.0625"×1"×4" (type 304) were dip coated in a 10 wt. percent of PSF-SR solution using methylene chloride as a solvent. The PSF-SR had an R.V. of 0.45. After air drying for 1 hour and oven drying for 10 minutes at 110° C. the samples were subsequently dip coated again in a 15 wt. percent solution of P-3703, a lower mol. wt. polysulfone, in methylene chloride, air dried 1 hour, oven dried 110° C. for 15 minutes. The samples were then baked in a hot air oven for 5 minutes at 245° C. - removed and immediately were powder coated with 40 mesh powdered P-3703 polysulfone, using a tapped sieve. The samples were then clamped together to form lap-shear test specimens and placed in a 240 C. hot air oven for ½ hour to fuse. The same procedure was repeated only P-1700 powdered (40 mesh) resin was sifted over the primed, hot sample plates. The samples were then tested in lapshear following ASTM D1002-72 method. In table III below the results obtained are set forth:

TABLE III

| Thermoplastic | Shear Strength (psi) | Type of Failure |
|---|---|---|
| P-3703 | 1596 | Cohesive |
| P-3703 | 1435 | Cohesive |
| P-1700 | 1407 | Cohesive |
| P-1700 | 1340 | Cohesive |

EXAMPLE VI
Shear Strength Measurements of Reinforced Porous Bioengineering Thermoplastics Stainless steel strips (type 304) 0.0625"×1"×4" were washed in hexane followed by isopropanol and dried. The strips were then dip coated in a 10% by wt. polysulfone SR (R.V. 0.517) methylene chloride solution using a mechanical dipping motor which provided a uniform rate of withdrawal from the solution of the stainless strip of 4"/1½ minutes. The strips were air dried at room temperature for 2 hours and then hot air oven baked at various temperatures for ½ hour. After drying, the specimens were spaced 3/16" apart with shims, clamped together and a 15% by wt. carbon fiber filled polysulfone/$CH_2Cl_2$/$H_2O$ dough was inserted between the stainless plates. The assembly was placed in a hot air oven at 150° C. for 15 minutes to foam the "dough" and bond it to the metal plates. The samples were then tested in lap shear following the ASTM D1002-72 method. The results obtained are set forth in Table IV below:

TABLE IV

| Coating Cure T °C. | Shear Strength (psi) | Type of Failure |
| --- | --- | --- |
| R.T. air dry | 245.2 | Adhesive |
| 190° C. 10 min. | 428.5 | Adhesive 25% Cohesive 75% |
| 240° C. 10 min. | 444 | Cohesive |

The same procedure was repeated to coat identical stainless steel strips using a 10 wt. percent solution of P-1700 polysulfone in methylene chloride. The results obtained are set forth in Table V below:

TABLE V

| Coating Cure T °C. | Shear Strength (psi) | Type of Failure |
| --- | --- | --- |
| R.T. air dry |  | (coating peeled off) |
| 190° C. 10 min. | 113.1 | Adhesive |
| 240° C. 10 min. | 340 | Cohesive |
| 320° C. 10 min. | 410 | Cohesive |

EXAMPLE VII

Comparative Creep Modulus Data on Thermoplastics

In order to demonstrate the differences in creep modulus at 75° C. for the bioengineering thermoplastics of this invention and other materials, data was compiled as is set forth in Table VI below:

TABLE VI

| Material | Initial Applied Stress p.s.i. | Creep (apparent) modulus thousand p.s.i. | | |
| --- | --- | --- | --- | --- |
| | | 1 hr. | 100 hr. | 1000 hr. |
| ENGINEERING PLASTICS | | | | |
| Astrel 360* | 8200 | 2730 | 1365 | |
| ICI 300 P* | 4000 | 350 | 320 | 310 |
| UDEL P-1700* | 4000 | 345 | 340 | 325 |
| LEXAN 141-111** | 3000 | 345 | 320 | 310 |
| OTHER MATERIALS | | | | |
| Diaken MG 102*** | 1450 | 386 | 269 | N.A. |
| MARLEX 6050**** | 1500 | 30 | 7.5 | N.A. |
| Stamylan 9309**** | 1075 | 170 | 80 | 31 |
| Profax 6423***** | 1500 | 104 | 58 | 37 |
| Propathene GWM 201***** | 725 | 104 | 56 | 41 |

*Polysulfone
**Polycarbonate
***PMMA
****HDPE
*****Polypropylene

Although the invention has been illustrated by the preceding examples, it is not to be construed as being limited to the materials employed therein, but rather the invention relates to the generic area as hereinbefore disclosed. Various modifications and embodiments can be made without departing from the spirit and scope thereof.

What is claimed is:

1. A process for the preparation of a sintered bioengineering thermoplastic material wherein both porosity and mechanical strength are optimized, said process comprising the steps of:
    (a) forming a mixture of at least one sinterable bioengineering thermoplastic material selected from the group consisting of polysulfones, polyphenylenesulfides, polyacetals, thermoplastic polyesters, polycarbonates, aromatic polyamides, aromatic polyamideimides, thermoplastic polyimides, polyaryletherketones, polyarylethernitriles and aromatic polyhydroxyethers, in particular form, said mixture having at least one fraction of a biomodal distribution of average particle diameters of from about 7:1 to about 5:1,
    (b) heating said mixture at a temperature and time sufficient to sinter the components of said mixture to produce a porous product which does not rely on another component for its structural integrity said porous product having:
        (a) an average pore diameter of about 90 to about 600 microns;
        (b) pore interconnection having average diameters fo greater than about 50 microns; and
        (c) a porosity f greater than about 25 percent, and
    (c) recovering using said product as a prosthesis.
2. The process of claim 1 wherein said mixture contains a sintering additive in an amount sufficient to lower said temperature and/or shorten said time necessary to prepare said sintered material.

* * * * *